United States Patent [19]
Lemieux

[11] Patent Number: 5,084,023
[45] Date of Patent: Jan. 28, 1992

[54] BLOODLESS CATHETER WITH SELF-SHIELDING NEEDLE

[75] Inventor: Francis P. Lemieux, Palm Harbor, Fla.

[73] Assignee: Critikon, Inc., Tampa, Fla.

[21] Appl. No.: 497,031

[22] Filed: Mar. 22, 1990

[51] Int. Cl.⁵ .................................... A61M 5/178
[52] U.S. Cl. ........................ 604/167; 604/93; 604/33; 604/202; 604/205; 604/249; 604/283; 604/905; 604/164
[58] Field of Search .............. 604/33, 34, 43, 44, 604/93, 164, 167, 201, 202, 205, 239, 240, 249, 247, 256, 905, 283

[56] References Cited

U.S. PATENT DOCUMENTS

| | | |
|---|---|---|
| 4,349,023 | 9/1982 | Gross .................................. 604/164 |
| 4,430,081 | 2/1984 | Timmermans ....................... 604/167 |
| 4,518,383 | 5/1985 | Evans .................................. 604/164 |
| 4,576,199 | 3/1986 | Svensson et al. .................... 604/905 |
| 4,735,614 | 4/1988 | Yapp et al. .......................... 604/169 |
| 4,863,432 | 9/1989 | Kvalo ................................... 604/164 |
| 4,895,346 | 1/1990 | Steigerwald ......................... 604/167 |
| 4,929,235 | 5/1990 | Merry et al. ........................ 604/167 |
| 4,952,207 | 8/1990 | Lemieux .............................. 604/164 |

Primary Examiner—C. Fred Rosenbaum
Assistant Examiner—Chalin Smith
Attorney, Agent, or Firm—Paul A. Coletti

[57] ABSTRACT

A catheter with a double membrane gasket and a locking needle guard is disclosed. The gasket prevents blood from seeping through the catheter hub. The locking needle guard prevents the user from inadvertent needle sticks.

24 Claims, 2 Drawing Sheets

BLOODLESS CATHETER WITH SELF-SHIELDING NEEDLE

FIELD OF THE INVENTION

This invention relates to intravascular (I.V.) catheters and, in particular, to I.V. catheter assemblies which cover the needle point after use to prevent accidental injury from used needles.

BACKGROUND OF THE INVENTION

Intravenous catheters for the infusion of fluids into the peripheral veins of a patient are one of the most common devices used in I.V. therapy. I.V. catheters may be produced in two general forms: through-the-needle catheters, in which a catheter is threaded through the needle cannula and into the vein of a patient, and over-the-needle catheters, in which the needle and concentric outer catheter are inserted into the vein and the needle is withdrawn through the emplaced catheter.

A typical over-the-needle I.V. catheter assembly requires the user to remove and then dispose of a contaminated needle after the needle tip and catheter are properly located in a blood vessel of a patient. Once the needle is withdrawn from the catheter, the user's immediate priorities are infusion set connection and site preparation, including the taping of the catheter to the patient. Because of the urgency of these procedures, the needle is normally just dropped conveniently nearby and then retrieved later. Since the needle at this time is exposed and located close to where the user is completing work with the catheter, accidental self-inflicted needle injuries are not uncommon. For reasons of the desirability of protecting the user from exposure to blood borne disease such as hepatitis and AIDS, there is an increasing need to protect the user from accidental needle injury.

A catheter design which is directed toward this need is shown in U.S. Pat. No. 4,762,516. The catheter shown in this application includes an elongate body which houses a sliding needle guard. In use, the needle with its surrounding catheter tube is inserted through the skin of a patient until the tip of the needle is located in a blood vessel, a position detected by a small flow of blood through the needle and into the flash chamber of the catheter. The user then advances a tab on the top of the needle guard to simultaneously thread the catheter tube into the blood vessel and begin the retraction of the needle from the catheter tube. As the needle is withdrawn from the emplaced catheter, the advance of the tab slides the needle guard out of the housing and along the needle, until the distal end of the guard covers the needle tip and the proximal end of the guard locks in a slot in the cannula. The needle and guard may then be set aside with the needle tip fully protected.

SUMMARY OF THE INVENTION

Accordingly, it is an object of the invention to provide a catheter in which the needle or cannula may be removed through the catheter without entry of blood into the catheter device, especially into the flash-chamber of the catheter.

It is yet another object of the invention to provide a catheter in which the cannula is protected throughout withdrawal from the catheter hub and is locked into a guard after withdrawal from the catheter hub.

It is yet another object of the invention to provide a system whereby the infusion line is movable into place through the catheter hub without fear of any accumulated blood to seep from the catheter hub.

It is another object of the invention to provide a holding chamber where any blood which enters the catheter while following the removed cannula is prevented from seeping any further into the catheter hub assembly.

Finally, it is an object of the invention to provide a catheter assembly where the catheter and needle assembly are formed in a two-piece system which has a barrier element in place between these pieces and allows the user to selectively move from needle placement to infusion.

These and other objects of the invention are accomplished in a bloodless, stickless, self-shielding catheter as described in this application. The catheter has a two-piece needle and catheter assembly with a locking needle guard and a return valve containing a gasket to eliminate blood leakage. Upon insertion of the needle through the needle guard and through the valve membrane in order to enter the catheter hub, the valve membrane is held in place and the needle is ready for use. After insertion of the needle (inside the catheter) into the patient, the needle is now ready to be removed. During removal the needle encounters a locking mechanism which automatically locks the end of the needle to the needle guard. The needle with needle guard locked in place over the needle tip is then removable from the catheter hub assembly.

The catheter hub has a return valve with a gasket which seals any blood flow from the catheter hub after removal from the needle, by means of the materials chosen for the gasket and the location of the gasket on the catheter hub assembly. A side port connector remotely connects an infusion line and is moved into place so that the area on the gasket into which the needle is originally placed for insertion into the catheter is not exposed to the catheter during infusion, and the gasket holds the remaining blood which has entered the system.

These and other objects of the invention are accomplished in connection with the following detailed description of the drawings and detailed description of the invention.

DETAILED DESCRIPTION OF THE DRAWINGS

DETAILED DESCRIPTION OF THE DRAWINGS

Figure 1:
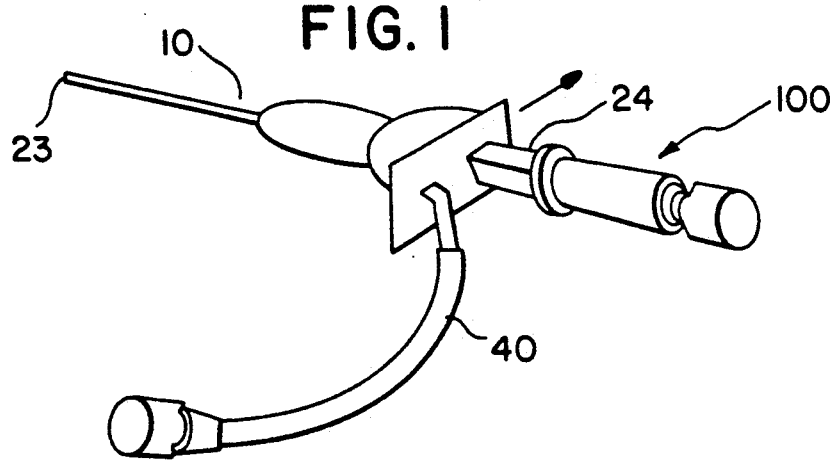
FIG. 1 is a perspective view a catheter and needle assembly as disclosed in this invention.

As seen in the Figures, the catheter 100 of this invention has three basic components: a catheter assembly 10, a needle assembly 20, and a valve assembly 30. The catheter assembly 10 is composed of a catheter 12 attached to a catheter hub 14. Both the catheter 12 and catheter hub 14 are essentially tubular in shape and hollow through the center. The catheter assembly 10 contains a distal connection 16 for the valve assembly 30 of the current invention and the catheter 12 of this invention is able to be inserted over the needle 22, then into the patient.

Figure 5:
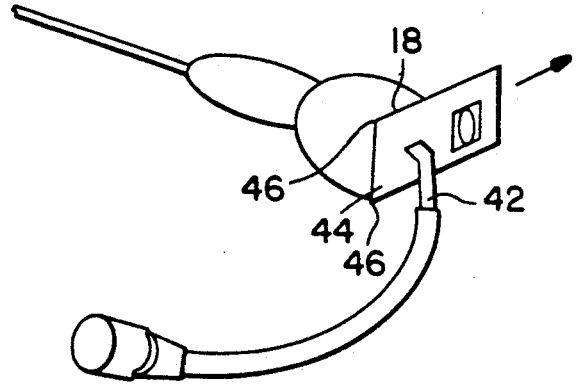
FIG. 5 is a perspective view of the remote side port catheter hook up assembly.
Figure 6A:
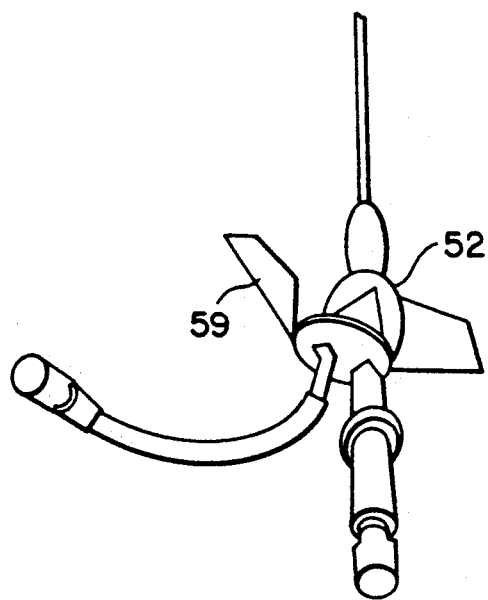
FIGS. 6a and 6b are perspective views of an alternate embodiment of the remote side port hook up assembly.
Figure 6B:
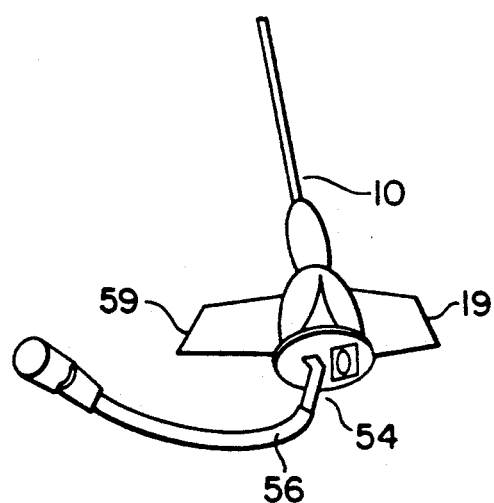

Briefly, the needle assembly 20 of the invention contains a needle 22 which is centrally located within a needle guard 24 and needle hub 26. The needle 22 is slidable relative to both the needle guard 24 and needle hub 26 so that it extends distally from the needle assembly 20. The needle 22 is inserted into the catheter assembly 10 to fit snugly within the catheter 12. At its longest extension, the tip 23 of the needle 22 is exposed outside the catheter 12 so that it is ready for insertion into the patient. Thus, the catheter assembly 10 with the valve assembly 30 and needle assembly 20 attached and the needle 22 exposed through the catheter 12 is placed in the patient. Then, the needle 22 is removed and infusion supply can be provided to the patient from the side port hook up assembly 40 as shown in FIGS. 5, 6a and 6b.

As previously described there are two intrisic problems with use of over-the-needle catheters. First, after the removal of the needle 22 from the catheter 12, there is some possibility that blood from the patient will seep through the catheter 12 following the removed needle and into the area in which infusion is provided from the hook up assembly. Second, there is the problem with disposal of the used needle 22. Especially if there is difficulty with the blood seepage from catheter assembly 10, the problem of needle 22 disposal becomes less focused and consequently more acute.

Figure 3A:
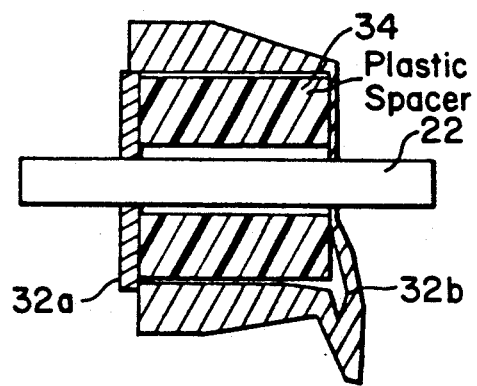
FIGS. 3a and 3b are cross-sectional views of the catheter valve assembly.
Figure 3B:
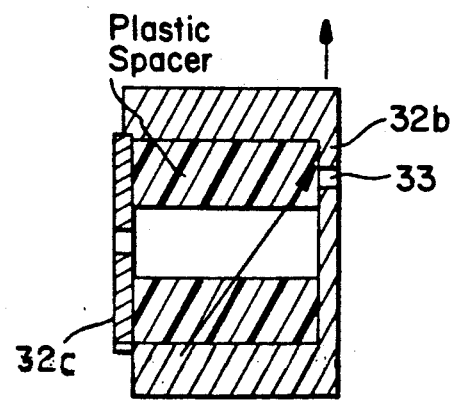

One of these difficulties is avoided by use of the valve assembly 30 of the present invention. As seen in FIGS. 3a and 3b, the gasket contained in valve assembly 30 includes a double chambered membrane 32a, 32b which allows the user to remove the needle 22 without danger of blood following the needle 22 through the catheter 12 and into the side port hook up 42. At its proximal end 32a, the gasket valve forms a first membrane, which is made from latex or any equivalent material and provides a basic fluid seal around the needle 22 during insertion into the catheter 12. This first membrane 32a is placed on the valve assembly 30 proximal to a plastic spacer 34 and within the catheter hub 14. The second membrane 32b is placed around the plastic spacer 34 and is formed from a latex cap which is held in place between the plastic spacer 34 and the needle assembly 20.

Upon insertion of the needle 12 from the needle assembly 20 into the catheter assembly 10, the second membrane 32b is pulled by the user so that the membrane 32b is displaced through the area of needle channel 36. In this way, when the needle 22 is inserted into the catheter 12, the needle 22 must first pierce the second membrane 32b. Optionally, to insure user compliance a slidable fitted polymeric member (not shown) can be incorporated over second membrane 32b. This polymeric membrane contains a central hole through which needle 22 may be inserted. The needle 22 pierces membrane 32b at a point removed from where the second membrane 32b would normally be positioned in its relaxed position. The needle 22 then pierces the first membrane 32a and is then inserted into the catheter 12.

After the needle 22 is inserted into the patient and then ready to be removed, the needle 22 is removed through the first membrane 32a. The first membrane 32a at that point stops nearly all the blood at the latex seal formed at the first membrane 32a. While most of the blood is sealed from the space created between the plastic spacer 34 in the valve assembly 30, some blood will weep due to compression set around the hole 31 made by the needle 22, and seep into the area of the plastic spacer 34.

At that point that the second membrane 32b takes control to seal the fluid path. After the needle 22 is pulled from the second membrane 32b, the elasticity of the membrane 32b snaps membrane 32b into its original shape. The pierced hole 33 moves away from the center of the valve assembly 30 and out of line with chamber 36 in plastic spacer 34. Thus, the spacer 34 seals the hole from any weeped blood in the fluid path of the valve assembly 30, so that blood is trapped. Thus, there is no danger of blood entering into the needle assembly 20 or side port 40 after removal by the user. Also, the needle 22 has been almost entirely wiped because of the pull of the needle 22 through the two membranes 32a, 32b.

Figure 2:
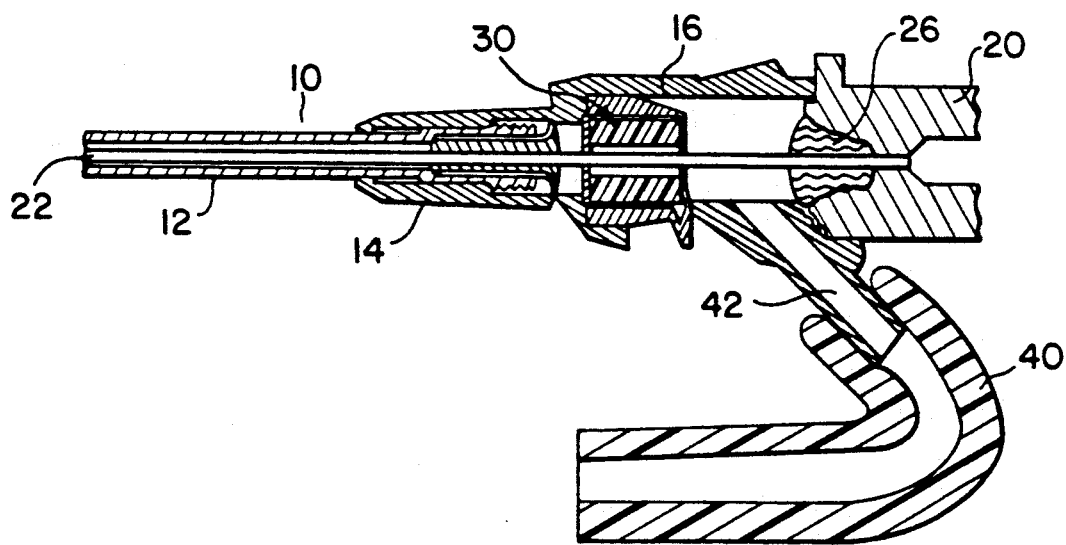
FIG. 2 is a cross-sectional view of the needle and catheter assembly of FIG. 1.
Figure 4:
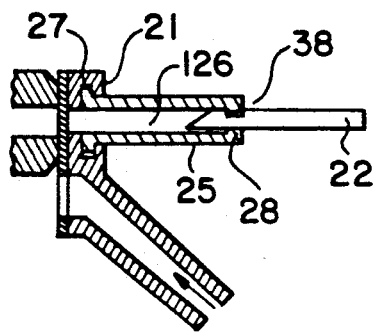
FIG. 4 is a cross-sectional view of the needle guard locking assembly.

At that point, the second problem is encountered, that is, disposal of the used needle 22. As seen in FIGS. 1, 2 and 4, this problem is attended to by the needle guard 24 of this invention. In this way, after the needle 22 is removed from the bloodless return valve assembly 30 as previously described, the needle 22 is placed into a chamber 126 within the needle guard 24. The needle guard 24 comprises a sleeve 25 with a ring 28 around its distal end which fits into the slot 38 seen in the rear of the valve assembly 30. Thus, the needle guard 24 is kept in place through insertion and removal of the needle 22 into the catheter assembly 10. The needle 22 itself as seen in FIG. 4 has a notched locking mechanism 21. This notched locking mechanism is formed in mating relationship with the tab 27 on the needle guard 24. In this way, after the needle 22 is removed from the catheter hub 14, the needle 22 is made to be pulled almost the entire length through the needle guard 24. The notch 21 on the cannula or needle 22 is placed into mating relationship with the tab 27 on needle guard 24. The needle guard 24 is thus locked in place on the end of the needle 22. The needle guard 24 can be slid out of the rear of valve assembly 30 so that the needle 22 can be safely and easily disposed, as seen in FIG. 4.

It is at that point that the mechanism which provides nourishment and/or drug supply can be slid into place. As seen in FIGS. 5, 6a and 6b, this mechanism may be formed in two different ways. First, a side assembly 40 may be slid into place allowing the side port connector 42 to be moved into place over the catheter and valve assemblies 10, 30. This may take place through a sliding mechanism 44 provided on the back of the valve and catheter assembly 30, 10, as seen in FIG. 5. When the needle 22 is removed, there is no resistance and the side port connector 44 can be moved into place. Upon placing the side assembly 40 into place, the side assembly 40 locks into place by the tabs 46 in the side assembly 40 locking into place within the notches 18 in the catheter assembly 10.

Alternately, infusion can be provided rotationally as seen in FIGS. 6a and 6b. There, originally, the needle 22 is rotatably in place so that the needle 22 is insertable into the catheter assembly 10. This is most readily seen as in FIG. 6a. After removal of the needle 22, the needle assembly 20 with needle 22 removed is made to rotate about the catheter assembly 10 at pivot point 52. At this pivot point 52, a side port connector 54 moves into place, and wing 19 on the catheter assembly 10 comes parallel with wing 59 on needle assembly 20. These wings 19, 59 are taped to the patient during infusion through the side port assembly 50.

Of course, on the side port assembly 50, there may be provided a luer locking assembly rather than the presently disclosed tube 56 which fits in a mating relationship over the side port 54 as seen in FIG. 6b. What is necessary is a mating gasket relationship so that infusion can take place.

These and other aspects of the invention have been described herein. It is to be understood that the above invention is to be determined from the attached claims and their equivalents.

What is claimed is:

1. A catheter assembly comprising:
    a catheter attached to a catheter hub;
    a double membrane emplaced in said catheter hub comprising a first membrane and a second membrane separated by a chamber having a longitudinal axis, said second membrane slidable in a direction transverse to said longitudinal axis;
    a needle insertable into said catheter through said catheter hub;
    a needle guard attached to said catheter hub wherein said needle is insertable through said needle guard into said catheter hub; said needle slidable relative to said needle guard, catheter hub and catheter through said longitudinal axis; and
    locking means preventing removal of said needle from said needle guard.

2. The catheter assembly of claim 1 further comprising said needle guard having a tubular configuration and said needle insertable within said needle guard in a mating relationship, said needle containing a notch on which to lock said needle guard.

3. The catheter assembly of claim 2 wherein said needle guard contains a tab capable of locking on said notch.

4. The catheter assembly of claim 3 wherein said needle guard is removable from said catheter hub.

5. The catheter assembly of claim 4 wherein said needle guard and catheter hub are slidable in relation to each other and said needle guard is held on said catheter hub in locked relationship when said needle is inserted into said catheter.

6. The assembly of claim 5 wherein said needle guard is removably attached to a plate on said catheter hub, said plate holding a side port connector.

7. The assembly of claim 6 wherein said connector is rotatable into a position on said catheter hub wherein an infusion set is capable of supplying solution through said catheter.

8. The assembly of claim 6 wherein said connector is slidable into position on said catheter hub wherein an infusion set is capable of supplying solution through said catheter.

9. The assembly of claim 7 wherein said catheter hub and said plate each contain a wing aligned with one another and wherein said side port provides infusion to said catheter.

10. The assembly of claim 8 wherein said catheter hub and said plate each contain a wing for attachment to a patient.

11. A catheter assembly comprising:
    an insertion needle;
    a catheter attached to a catheter hub;
    a gasket in said catheter hub and containing a double membrane separated by a chamber, said chamber having a longitudinal axis;
    said needle insertable into said catheter though said double membrane and across said chamber along said longitudinal axis;
    wherein said double membrane comprises a first membrane and second membrane separated by said chamber, and said second membrane is slidable in a direction transverse to the longitudinal axis of said chamber.

12. The catheter assembly of claim 11 further comprising said needle insertable into a needle guard, said needle guard insertable into said catheter hub; said needle further comprising locking means capable of locking said needle to said needle guard.

13. The catheter assembly of claim 1 wherein said needle further contains a notch along the side of said needle, said notch locking on said needle guard.

14. The catheter assembly of claim 13 wherein said needle guard contains a tab, said tab insertable into said needle notch.

15. The catheter assembly of claim 14 wherein said needle guard is removable from said catheter hub.

16. The assembly of claim 11 wherein said needle pierces said second membrane upon the sliding of said second membrane relative to said chamber.

17. The assembly of claim 16 wherein said second membrane has a memory to return to a relaxed position upon the removal of said needle.

18. The assembly of claim 11 wherein said needle is insertable into said first membrane and seals upon the removal of said needle from said catheter hub and said first membrane.

19. The catheter assembly of claim 11 wherein said double membrane further comprises a spacer containing said chamber for insertion of said needle.

20. The catheter assembly of claim 19 wherein said second membrane is movable relative to said spacer in order to be pierced by said needle.

21. The catheter assembly of claim 20 wherein said second membrane retracts to a relaxed position upon the removal of said needle.

22. The catheter assembly of claim 21 wherein a said first and second membranes are comprised of latex.

23. The catheter assembly of claim 21 wherein said first membrane closes upon the retraction of said needle.

24. The catheter assembly of claim 21 wherein said second membrane is attached to a slidable member movable relative to said spacer in order to insert said needle into said slidable member and said second membrane.

* * * * *